(12) United States Patent
Ulmius

(10) Patent No.: US 6,423,340 B1
(45) Date of Patent: Jul. 23, 2002

(54) METHOD FOR THE TREATMENT OF INFLAMMATORY BOWEL DISEASES

(75) Inventor: Jan Ulmius, Lund (SE)

(73) Assignee: Aktiebolaget Draco, Sodertalje (SE)

( * ) Notice: Subject to any disclaimer, the term of this patent is extended or adjusted under 35 U.S.C. 154(b) by 0 days.

(21) Appl. No.: 09/159,301

(22) Filed: Sep. 23, 1998

Related U.S. Application Data

(63) Continuation of application No. 08/853,142, filed on May 8, 1997, now abandoned, which is a continuation of application No. 08/240,078, filed on May 9, 1994, now Pat. No. 5,643,602, which is a continuation of application No. 07/855,623, filed as application No. PCT/SE90/00738 on Nov. 15, 1990, now abandoned.

(30) Foreign Application Priority Data

Nov. 15, 1990 (SE) ................................. 8903914

(51) Int. Cl.$^7$ ........................... A61K 9/52; A61K 9/22; A61P 1/00
(52) U.S. Cl. ..................... 424/457; 424/468; 424/490; 514/925; 514/964
(58) Field of Search ................................ 424/462, 457, 424/468, 490; 514/964, 925

(56) References Cited

U.S. PATENT DOCUMENTS

| | | |
|---|---|---|
| 3,983,233 A | 9/1976 | Brattsand et al. |
| 3,996,356 A | 12/1976 | Brattsand et al. |
| 4,432,966 A | 2/1984 | Zeitoun et al. |
| 4,606,940 A | 8/1986 | Frank et al. |
| 4,708,867 A | 11/1987 | Hsiao |
| 4,966,770 A | 10/1990 | Giannini et al. |

FOREIGN PATENT DOCUMENTS

| | | |
|---|---|---|
| EP | 0013262 | 7/1980 |
| EP | 0040590 | 5/1981 |
| EP | 1480811 | 1/1985 |
| EP | 0054010 | 2/1985 |
| EP | 0143764 | 6/1985 |
| EP | 0278174 | 8/1986 |
| EP | 0232690 | 8/1987 |
| EP | 0218174 | 12/1987 |
| WO | 8300435 | 2/1983 |
| WO | 8603676 | 12/1985 |

OTHER PUBLICATIONS

Manufacturer's Info. (FMC Corporation) re: Aquacoat (ethylcellulose), "Altering Drug Release Rates–Coating Methods" (1987).
Manufacturer's Info. Re: Aquacoat (ethylcellulose), 17–36 (1985).
Manufacturer's Info. Re: Eudragit, Lehmann, et al., "Practical Course in Lacquer Coating," 1–167 (1989).
Wolman, et al., Scand. J. Gastroenterol. 24: 146–147 (1989).
Johansson, et al., Eur. J. Respir. Dis. 63: 74–84 (1982).
Bechgaard, Acta Pharmaceutica Technologica 28: 149–157 (1982).
Danielsson, et al., Scand. J. Gastroenterol. 22: 987–992 (1987).
Malchow, et al., Deutsche Medizinische Wochenschrift 1090: 1811–1816 (1984).
Andersson, et al., J. Steroid Biochem. 16: 787–795 (1982).
Kresznai, et al., Haematologia 19: 299–301 (1986).
Kumana, et al., Lancet 1: 579–583 (1982).
Levine, et al., Gastroenterol. 92: 1037–1044 (1987).
Thomas, et al., J. Pharm. Pharmacol. 37: 757–758 (1985).
Jewell, Gastroenterol. Clin. North America 18: 21–34 (1989).
Gamstedt, et al., Acta Endocrinologica 103: 188–191 (1983).
Hamilton, et al., Dis. Col. & Rect. 27: 701–702 (1984).
Ryrfeldt, et al., Eur. J. Respir. Dis. 63: 86–94 (1982).
Mulder, et al., Netherlands J. Med. 35: pp. S27–S34 (1989).
Malchow, et al., Gastroenterolgy 86: 249–266 (1984).

*Primary Examiner*—Edward J. Webman
(74) *Attorney, Agent, or Firm*—White & Case LLP

(57) ABSTRACT

Described herein are methods comprising the oral administration of budesonide for the treatment of ulcerative colitis and Crohn's colitis in its active phase. The methods can also be applied as relapse preventing therapy for Crohn's colitis in its chronic phase and Crohn's disease in the small intestine.

14 Claims, No Drawings

METHOD FOR THE TREATMENT OF INFLAMMATORY BOWEL DISEASES

This application is a continuation of application Ser. No. 08/853,142, field May 8, 1997, abandoned, which is a continuation of application Ser. No. 08/240,078, filed May 9, 1994, now U.S. Pat. No. 5,643,602 and which is a continuation of application Ser. No. 07/855,623, filed Apr. 30, 1992 abandoned, which is a 371 of International application PCT/SE90/00738, filed Nov. 15, 1990.

FIELD OF THE INVENTION

The present invention relates to oral pharmaceutical compositions for use in the treatment of inflammatory bowel diseases and the use of certain glucocorticosteroids in the preparation of pharmaceutical compositions for the treatment by the oral route of certain inflammatory bowel diseases.

BACKGROUND OF THE INVENTION

Inflammatory bowel disease is the term generally applied to two diseases, namely ulcerative colitis and Crohn's disease.

Ulcerative colitis is a chronic inflammatory disease of unknown aetiology afflicting only the large bowel and, except when very severe, limited to the bowel mucosa. The course of the disease may be continuous or relapsing, mild or severe. It is curable by total colectomy which may be needed for acute severe disease or chronic unremitting disease. Most patient with ulcerative colitis are managed medically rather than surgically.

Crohn's disease is also a chronic inflammatory disease of unknown aetiology but, unlike ulcerative colitis, it can affect any part of the bowel. Although lesions may start superficially, the inflammatory process extends through the bowel wall to the draining lymph nodes. As with ulcerative colitis, the course of the disease may be continuous or relapsing, mild or severe but, unlike ulcerative colitis it is not curable by resection of the involved segment of bowel. Most patients with Crohn's disease come to surgery at some time, but subsequent relapse is common and continuous medical treatment is usual.

For treatment of acute attacks of ulcerative colitis, glucocorticosteroids such as prednisone or prednisolone acetate are almost invariably used and given by mouth for the average acute attack or relapse, or locally, by enema.

After remission has been achieved, sulphasalazine is the maintenance treatment of choice in treating ulcerative colitis. This drug, however, has a significant number of side effects chiefly due to absorption of the sulphapyridine moiety from the colon. Recently compounds which contain only 5-aminosalicylic acid have been developed; these are as effective as sulphasalazine and do not have the sulphapyridine side effects but do have side effects of their own, notably diarrhoea.

Glucocorticosteroids are, however, not used for maintenance of remission in ulcerative colitis; doses that do not produce unacceptable side effects are ineffective, and patients who need chronic high dose glucocorticosteroids for control of their disease almost invariably are treated by colectomy.

As with ulcerative colitis, glucocorticosteroids are the treatment of choice for severe active Crohn's disease, but ideally only to achieve remission, after which they should be stopped. However, all too frequently the disease does not satisfactorily remit, and glucocorticosteroids may be necessary to maintain control of symptoms.

Sulphasalazine is also useful in less severe cases, particularly for disease involving the colon.

Very often in Crohn's disease, however, primary medical treatment of the disease process is ineffective, and only symptomatic treatment is of value i.e. analgesics for pain and opiates for diarrhoea. Most patients eventually require surgery.

DISCLOSURE OF THE INVENTION

Our studies indicate that the compositions according to the present invention may advantageously be used in the treatment of ulcerative colitis including idiopathic proctitis and certain aspects of Crohn's disease by the oral route.

In ulcerative colitis the compositions can be used for the treatment of both active and chronic continuous disease and for relapse preventing treatment (i.e. maintenance therapy once remission has been achieved).

In Crohn's disease the compositions can be used for the treatment of Crohn's colitis in its active phase and for relapse preventing therapy (i.e. maintenance therapy once remission has been achieved), and for the treatment of the small intestine for relapse preventing treatment (i.e. maintenance therapy).

It has been found that the diseases defined above can be treated using the anti-inflammatory steroids (22RS)-16α,17α-butylidenedioxy-11β,21-dihydroxypregna-1,4-diene-3,20-dione [I],
the 22R-epimer of [I],
(22RS)-16α,17α-butylidenedioxy-9α-fluoro-11β,21-dihydroxy-pregna-1,4-diene-3,20-dione [II],
the 22R-epimer of [II],
(22RS)-16α,17α-butylidenedioxy-6α,9α-difluoro-11β,21-dihydroxy-pregna-1,4-diene-3,20-dione [III],
the 22R-epimer of [III],
(22RS)-21-acetoxy-16α,17α-butylidenedioxy-11β-hydroxy-pregna-1,4-diene-3,20-dione [IA],
the 22R-epimer of [IA],
(22RS)-21-acetoxy-16α,17α-butylidenedioxy-9α-fluoro-11β-hydroxy-pregna-1,4-diene-3,20-dione [IIA],
the 22R-epimer of [IIA],
(22RS)-21-acetoxy-16α,17α-butylidenedioxy-6α,9α-difluoro-11β-hydroxy-pregna-1,4-diene-3,20-dione [IIIA],
the 22R-epimer of [IIIA],
(22RS)-16α,17α-butylidenedioxy-11β,21-dihydroxypregn-4-ene-3,20-dione [IV],
the 22R-epimer of [IV],
(22RS)-16α,17α-pentylidenedioxy-11β,21-dihydroxypregn-4-ene-3,20-dione [V],
the 22R-epimer of [IV],
(22RS)-21-acetoxy-16α,17α-butylidenedioxy-11β, hydroxypregn-4-ene-3,20-dione [IVA],
the 22R-epimer of [IVA],
(22RS)-21-acetoxy-16α,17α-pentylidenedioxy-11β,21-dihydroxypregn-4-ene-3,20-dione [VA],
the 22R-epimer of [VA],
methyl (20RS)-16α,17α-butylidenedioxy-11β-hydroxy-androsta-1,4-diene-3-one-17β-carboxylate [VI],
the 20R-epimer of [VI],
methyl (20RS)-16α,17α-butylidenedioxy-9α-fluoro-11β-hydroxy-androsta-1,4-diene-3-one-17β-carboxylate [VII],
the 20R-epimer of [VII], methyl (20RS)-16α,17α-butylidenedioxy-6α,9α-difluoro-11β-hydroxy-androsta-1,4-diene-3-one-17β-carboxylate [VIII], the 20R-epimer of [VIII], methyl (22RS)-16α,17α-butylidenedioxy-6α,9α-difluoro-11β-hydroxy-3,20-dioxopregna-1,4-diene-21-oate [IX] and the 22R-epimer of [IX].

Compound [I] has the approved name "budesonide".

Compound [I] and its 22R-epimer are particular preferred compounds.

Budesonide and compounds [II], [III], [IA], [IIA] and [IIIA] are described and claimed in Swedish Patent Specification 378 109. Budesonide is known to have an anti-inflammatory activity and, compared to prednisone, prednisolone and other glucocorticosteroids, an advantageous ratio between local and systemic effect when administered topically to the skin or to the lungs by inhalation.

Budesonide is a potent steroid, which is successfully used when locally treating (via aerosol) asthma and rhinitis. Also controlled trials of budesonide enema for locally treating proctitis and distal ulcerative colitis are in progress (Danielsson Å et al: A controlled randomized trial of budesonide versus prednisolone retention enemas in active distal ulcerative colitis, Scand. J. Gastroenterol. 22:987–992, 1987 and Danielsson Å et al: Controlled trial of budesonide enema and placebo in proctitis and distal ulcerative colitis. Scand. J. Gastroenterol. 24. supplement 159:88). The use of oral budesonide in the treatment of small bowel Crohn's disease in its active phase has been described (Wolman S L: Use of oral budesonide in a patient with small bowel Crohn's disease and previous pseudotumor cerebri secondary to steroids. Scand. J. Gastroenterol. 24, Supplement 158:146–147).

The characteristic profile of budesonide when used for the treatment of these diseases is a high anti-inflammatory effect at the place of application but a low degree of unwanted systemic glucocorticoid side effects. The low degree of systemic side effects of budesonide is a result of a high first pass liver metabolism transferring budesonide into substantially less active metabolites.

Especially the 22R-epimer of budesonide seems to be very promising in the treatment of inflammatory bowel diseases as hereinbefore defined when orally administered because, compared to budesonide it is more potent, is more rapidly metabolised by the liver and thus less available in the systemic circulation and thereby causing less unwanted systemic effects.

The 22R-epimers of compounds [I], [II], [III], [IA], [IIA] and [IIIA] are described and claimed in Swedish Patent Specification 378 110.

Compounds [IV], [V], [IVA], [VA] and the 22R-epimers thereof are described and claimed in European Patent Specification 54010.

Compounds [VI], [VII], [VIII] and the 20R-epimers thereof are described and claimed in European Patent Application 143 764.

Compound [IX] and the 22R-epimer thereof are described and claimed in European Patent Application 232 690.

We have surprisingly found that the above identified glucocorticosteroids administered by the convenient oral route are of great potential benefit in the treatment of inflammatory bowel diseases as hereinbefore defined.

The above mentioned compounds thus potentially represents a very significant advance over other glucocorticosteroids which exert their effects systemically and other drugs previously used for the management of Crohn's disease, particularly in avoiding the systemic side effects normally associated with glucocorticosteroid therapy. The high first pass liver metabolism of the drug renders possible its safe use in the maintenance therapy of the disease as well as achieving remission in the acute phase. Although Crohn's disease is not a very common condition, it is a chronic and often debilitating disorder that can benefit from a safer and more effective treatment.

In ulcerative colitis, the drug may help to reduce the number of patients having to undergo surgery and in addition, its lack of systemic effects makes it possible to use the drug for maintenance therapy once remission has been achieved.

The invention therefore provides pharmaceutical compositions comprising the glucocorticosteroids hereinbefore defined for use in the treatment by the oral route of bowel diseases as hereinbefore defined.

The invention also provides the use of the glucocorticosteroids as hereinbefore defined in the preparation of pharmaceutical compositions for the treatment by the oral route of bowel diseases as hereinbefore defined.

The invention further provides a method of treatment of bowel diseases as hereinbefore defined wherein an effective dose of a glucocorticosteroid as hereinbefore defined is administered by the oral route to a human or animal subject suffering from said bowel disease.

In order for the oral composition containing the glucocorticosteroids as hereinbefore defined to be applicable for the treatment of the bowel diseases as hereinbefore defined the composition must be adjusted to this particular purpose. The adjusted composition is a further aspect of the present invention, and it can be used generally when treating ulcerative colitis and Crohn's disease.

The transit time through the gastro-intestinal canal for different dosage forms are rather well known. When the dosage form has been emptied from the stomach the transit through the small intestine takes 3 to 5 hours. The residence time in the large intestine is considerably longer, 25 to 50 hours. Ideally, as long as the dosage form remains in the stomach no release should occur. If Crohn's disease in small intestine is going to be treated the release should continue during about 5 hours after the dosage form has left the stomach. If the large intestine is going to be treated the release should ideally start at caecum, and continue for up to 50 hours.

The present invention utilizes pharmaceutical formulation techniques to provide compositions of a glucocorticosteroid for treating the inflammatory diseases of the bowel as hereinbefore defined. The glucocorticosteroid must have a chance to reach the inflamed part of the bowel in sufficient concentration and for a sufficient long time to exert its local action, in the case of Crohn's disease the whole bowel or only the small intestine and in the case of ulcerative colitis the caecum, colon and the rectum.

A multiple unit composition in a capsule has been found suitable for fulfilling the above-mentioned demands. In ulcerative colitis, the composition should be formulated so that the glucocorticosteroid is released preferentially during the passage of the colon. In Crohn's disease in the ileum the composition should be formulated so that the glucocorticosteroid is released preferentially during the Passage of the small intestine. This can be accomplished by enteric and/or slow release coating of the units containing the glucocorticosteroid. Such formulations of glucocorticosteroids are novel.

The dosage range for treatment of the bowel diseases as hereinbefore defined is suitably 2–20 mg divided into 1 to 4 doses during a 24-hour period.

DETAILED DESCRIPTION

The units will have a size between 0.3 and 5 mm, preferably a size between 0.5 and 2 mm. The units will be administered in hard gelatine capsules, the size of which will depend on the dose administered.

Each unit comprises a core, a first layer on the core and a second layer on the first layer.

The core consists of a non-pareil seed to which the glucocorticosteroid is applied or a seed in which the glucocorticosteroid is homogeneously distributed. The excipients used to prepare the seeds comprise one or more of pharmaceutically acceptable materials, e.g. sugar, starch, microcrystalline cellulose, waxes and polymeric binding agents.

The first Layer on the non-pareil seeds comprises the glucocorticosteroid and a water-soluble or water-insoluble polymer which acts both as binder for the glucocorticosteroid and as a rate-limiting layer for release of the glucocorticosteroid. Such polymers may be selected from cellulose derivatives, acrylic polymers and copolymers, vinyl polymers and other high molecular polymer derivatives or synthetic polymers such as methylcellulose, hydroxypropylcellulose, hydroxypropylmethylcellulose, ethylcellulose, cellulose acetate, polyvinyl pyrrolidone, polyvidone acetate, polyvinyl acetate, polymethacrylates and ethylene-vinyl acetate copolymer or a combination thereof. Preferred film-forming polymers are ethylcellulose or copolymers of acrylic and methacrylic acid esters (Eudragit N E, Eudragit R L, Eudragit RS) in aqueous dispersion form.

The first optionally rate-limiting layer on the seeds with homogeneously distributed glucocorticosteroid comprises a water insoluble polymer or a mixture of water insoluble polymers or a mixture of water soluble and water insoluble polymers mentioned above.

The polymers in the second layer may be selected from the group of anionic carboxylic polymers suitable for pharmaceutical purposes and being soluble with difficulty at a low pH but being soluble at a higher pH, the pH limit for solubility being in the interval of pH 4 to pH 7.5, said group comprising cellulose acetate phthalate, cellulose acetate trimellitate, hydroxypropylmethylcellulose phthalate, polyvinyl acetate phthalate and acrylic acid polymers e.g. partly asterified methacrylic acid-polymers such as Eudragit L, Eudragit L100-55 and Eudragit S. These polymers may be used alone or in combination with each other or in combination with water insoluble polymers mentioned before. Preferred polymers are the Eudragits in aqueous dispersion form. The anionic carboxylic polymer comprises 25 to 100% of the total polymer content.

The coatings may optionally comprise other pharmaceutically acceptable materials which improve the properties of the film-forming polymers such as plasticizers, anti-adhesives, surfactants, and diffusion-accelerating or diffusion-retarding substances.

Suitable plasticizers comprise phthalic acid esters, triacetin, dibutylsebacate, monoglycerides, citric acid esters and polyethyleneglycols. Preferred plasticizers are acetyltributyl citrate and triethyl citrate.

Suitable antiadhesives comprise talc and metal stearates.

The amount of the first coating applied on the units is normally in the range between 0.5% and 30% by weight, preferably between 1% and 15%. This amount includes in the relevant case the weight of the steroid as well. The amount of the second coating applied on the units is normally in the range between 1% and 50% by weight, preferably between 2% and 25%, calculated on the weight of the coated units. The remainder constitutes the weight of the seed.

The preparation of the controlled release pellet formulation according to the present invention is characterized in that a non-pareil seed is enclosed in a layer of a glucocorticosteroid as hereinbefore defined and a water soluble or water insoluble polymer or a seed with homogeneously distributed glucocorticosteroid as hereinbefore defined is optionally enclosed in a layer of a water insoluble polymer or a mixture of water insoluble polymers or a mixture of water soluble or water insoluble polymers which in turn is enclosed in a membrane of a film-forming anionic carboxylic polymer or a mixture of a film-forming anionic carboxylic polymer and a water insoluble polymer which permits release of the glucocorticosteroid as hereinbefore defined in a manner set out below.

The controlled release pellet formulation according to this invention is thus characterized in that the pellet comprises
i) a core consisting of a non-pareil seed or a seed in which a glucocorticosteroid as defined below is homogeneously distributed and
ii) in case of a core consisting of a non-pareil seed, a layer of
a) a glucocorticosteroid selected from the group consisting of (22RS)-16α,17α-butylidenedioxy-11β,21-dihydroxypregna-1,4-diene-3,20-dione [I], the 22R-epimer of [I], (22RS)-16α,17α-butylidenedioxy-9α-fluoro-11β,21-dihydroxy-pregna-1,4-diene-3,20-dione [II], the 22R-epimer of [II], (22RS)-16α,17α-butylidenedioxy-6α,9α-difluoro-11β,21-dihydroxy-pregna-1,4-diene-3,20-dione [III], the 22R-epimer of [III], (22RS)-21-acetoxy-16α,17α-butylidenedioxy-11β-hydroxypregna-1,4-diene-3,20-dione [IA], the 22R-epimer of [IA], (22RS)-21-acetoxy-16α,17α-butylidenedioxy-9α-fluoro-11β-hydroxy-pregna-1,4-diene-3,20-dione [IIA], the 22R-epimer of [IIA], (22RS)-21-acetoxy-16α,17α-butylidenedioxy-6α,9α-difluoro-11β-hydroxy-pregna-1,4-diene-3,20-dione [IIIA], the 22R-epimer of [IIIA], (22RS)-16α,17α-butylidenedioxy-11β,21-dihydroxypregn-4-ene-3,20-dione [IV], the 22R-epimer of [IV], (22RS)-16α,17α-pentylidenedioxy-11β,21-dihydroxypregn-4-ene-3,20-dione [VI], the 22R-epimer of [V], (22RS)-21-acetoxy-16α,17α-butylidenedioxy-11β-hydroxypregn-4-ene-3,20-dione [IVA], the 22R-epimer of [IVA], (22RS)-21-acetoxy-16α,17α-pentylidenedioxy-11β-hydroxypregn-4-ene-3,20-dione [VA], the 22R-epimer of [VA], methyl (20RS)-16α,17α-butylidenedioxy-11β-hydroxy-androsta-1,4-diene-3-one-17β-carboxylate [VI], the 20R-epimer of [VI], methyl (20RS)-16α,17α-butylidenedioxy-9α-fluoro-11β-hydroxy-androsta-1,4-diene-3-one-17β-carboxylate [VII], the 20R-epimer of [VII], methyl (20RS)-16α, 17α-butylidenedioxy-6α,9α-difluoro-11β-hydroxy-androsta-1,4-diene-3-one-17β-carboxylate [VIII], the 20R-epimer of [VIII], methyl (22RS)-16α,17α-butylidenedioxy-6α,9α-difluoro-11β-hydroxy-3,20-dioxo-pregna-1,4-diene-21-oate [IX] and the 22R-epimer of [IX] and
b) a pharmaceutical acceptable film forming water insoluble or water soluble polymer, or
in case of a core consisting of a seed in which a glucocorticosteroid as defined above is homogeneously distributed, an optionally layer of a pharmaceutically acceptable film forming water insoluble polymer or a mixture of water insoluble polymers or a mixture of water soluble and water insoluble polymers and iii) a membrane surrounding said core and layer and containing a pharmaceutically acceptable film-forming anionic carboxylic polymer being soluble with difficulty at low pH but being soluble at a higher pH, either alone or in combination with a pharmaceutically acceptable film-forming water insoluble polymer, the thickness of said layer or said membrane and/or the ratio of said anionic carboxylic polymer to said insoluble polymer being effective to prevent release of said glucocorticosteroid from said pellet in gastric fluids, but to permit release of said glucocorticosteroid from said pellet in intestinal fluids at a rate allowing treatment of the part of the intestinal tract where the disease resides, i.e. at a rate corresponding to a release time of 1 to 50 hours, preferably 5 to 10 hours when treating the small intestine and 25 to 50 hours when treating the large intestine, said rate being measured in vitro as a dissolution rate of said unit in simulated gastric and intestinal fluids, when measured in a flow through cell at 8 mL/min and 37° C. substantially corresponds to the following for units intended for treating the small intestine:

a) not more than 10%, preferably not more than 5%, of the total glucocorticosteroid is released after two hours in simulated gastric fluid in said assembly, b) from 15 to 55%, preferably from 20 to 50%, of the total glucocorticosteroid is released after two hours in simulated intestinal fluid in said assembly, c) from 35 to 80%, preferably from 40 to 70%, of the total glucocorticosteroid is released after four hours in simulated intestinal fluid in said assembly, d) not less than 60, preferably 60 to 90%, of the total glucocorticosteroid is released after eight hours in simulated intestinal fluid in said assembly, e) not less than 80% of the total glucocorticoid steroid is released after twelve hours in simulated intestinal fluid in said assembly, and for units intended for treating the large intestine:

a) not more than 10%, preferably not more than 5%, of the total glucocorticosteroid is released after two hours in simulated gastric fluid in said assembly, b) from 5 to 30%, preferably from 10 to 30%, of the total glucocorticosteroid is released after four hours in simulated intestinal fluid in said assembly, c) from 20 to 65%, preferably from 35 to 55%, of the total glucocorticosteroid is released after twelve hours in simulated intestinal fluid in said assembly, d) from 40 to 95%, preferably from 55 to 85%, of the total glucocorticosteroid is released after twenty-four hours in simulated intestinal fluid in said assembly, e) not less than 70%, preferably not less than 80%, of the total glucocorticosteroid is released after forty-eight hours in simulated intestinal fluid in said assembly.

In one embodiment of the composition there is a layer which comprises budesonide or the 22R epimer thereof and a water soluble or water insoluble polymer beneath the membrane surrounding the pellet.

In another embodiment of the composition the polymeric material of the layer in which budesonide or its 22R epimer is embedded is selected from polyvinylpyrrolidone and hydroxypropylmethylcellulose or alternatively from ethylcellulose, cellulose acetate and copolymers of acrylic and methacrylic acid esters.

In still another embodiment of the composition the layer which comprises budesonide or its 22R epimer and a water soluble or water insoluble polymer includes one or more additional components selected from plasticizers, anti-adhesives and surfactants.

WORKING EXAMPLES

The following pharmaceutical compositions can be used in the treatment of bowel diseases according to the invention.

EXAMPLE 1

|  | mg/capsule |
|---|---|
| Budesonide micronized | 1.0 |
| Sugar spheres | 321 |
| Aquacoat ECD 30 | 6.6 |
| Acetyltributyl citrate | 0.5 |
| Polysorbate 80 | 0.1 |
| Eudragit L100-55 | 17.5 |
| Triethylcitrate | 1.8 |
| Talc | 8.8 |
| Antifoam MMS | 0.01 |

Budesonide (32.2 g) was suspended in the Aquacoat ECD 30 dispersion (0.70 kg) with the aid of the Polysorbate 80 (0.42 g) together with acetyltributyl citrate (15.8 g). The mixture was sprayed on to sugar spheres (10.2 kg) in a fluid bed apparatus. The enteric coating consisting of the Eudragit L100-55 dispersion, (Eudragit L100-55 (0.558 kg), triethylcitrate (55.8 g), talc (0.279 kg), Antifoam MMS (0.44 g) and Polysorbate 80 (2.79 g) ) was then sprayed on the spheres. The pellets were dried in the fluid bed apparatus, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 1.4 g of pellets were placed in the cells and the test commenced. For specified time periods fractions were collected and analyzed for budesonide by a liquid chromatographic method. The percentage dissolution at each time point was calculated. The results are shown in Table 1.

TABLE 1

Dissolution of budesonide of Example 1

| Medium | Percentage dissolution after | | | | |
|---|---|---|---|---|---|
|  | 1 hour | 2 hours | 4 hours | 8 hours | 12 hours |
| SGF | 1 | 2 | 3 | — | — |
| SIF | 34 | 53 | 75 | 92 | 97 |

EXAMPLE 2

|  | mg/capsule |
|---|---|
| Budesonide micronized | 2.0 |
| Sugar spheres | 292 |
| Auquacoat ECD 30 | 4.8 |
| Acetyltributyl citrate | 0.4 |

-continued

|  | mg/capsule |
| --- | --- |
| Polysorbate 80 | 0.01 |
| Eudragit NE30D | 17.5 |
| Eudragit S100 | 17.5 |
| Talc | 17.5 |

Budesonide (3.5 g) was suspended in the Aquacoat ECD 30 dispersion (28.0 g) with the aid of the Polysorbate 80 (0.02 g) together with acetyltributyl citrate (0.63 g). The mixture was sprayed on to sugar spheres (510 g) in a fluid bed apparatus. The rate-limiting and enteric coating consisting of Eudragit S100 (30.0 g) and talc (30.0 g) suspended in the Eudragit NE30D dispersion (100 g) with the aid of Polysorbate 80 (0.3 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid and simulated intestinal fluid, 2.8 g of pellets were placed in the cells and the test commenced. For specified time periods fractions were collected and analyzed for budesonide by a liquid chromatographic method. The percentage dissolution at each time point was calculated. The results are shown in Table 2.

TABLE 2

Dissolution of budesonide of Example 2

| | Percentage dissolution after (hours) | | | | | | | | |
| --- | --- | --- | --- | --- | --- | --- | --- | --- | --- |
| Medium | 1 | 2 | 4 | 8 | 12 | 18 | 24 | 36 | 48 |
| SGF | 0 | 0 | 1 | — | — | — | — | — | — |
| SIF | 5 | 8 | 13 | 20 | 27 | 35 | 43 | 56 | 67 |

EXAMPLE 3

|  | mg/capsule |
| --- | --- |
| Budesonide micronized | 2.0 |
| Sugar spheres | 305 |
| Auquacoat ECD 30 | 5.0 |
| Acetyltributyl citrate | 0.4 |
| Polysorbate 80 | 0.14 |
| Eudragit NE30D | 12.6 |
| Eudragit S100 | 12.6 |
| Talc | 12.6 |

Budesonide (6.69 g) was suspended in the Aquacoat ECD 30 dispersion (56.0 g) with the aid of the Polysorbate 80 (0.04 g) together with acetyltributyl citrate (1.26 g). The mixture was sprayed on to sugar spheres (1020 g) in a fluid bed apparatus. The rate-limiting and enteric coating consisting of Eudragit S100 (42.0 g) and talc (42.0 g) suspended in the Eudragit NE30D dispersion (140 g) with the aid of Polysorbate 80 (0.42 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 2.1 g of pellets were placed in the cells and the test commenced. For specified time periods fractions were collected and analyzed for budesonide by a liquid chromatographic method. The percentage dissolution at each time point was calculated. The results are shown in Table 3.

TABLE 3

Dissolution of budesonide of Example 3

| | Percentage dissolution after (hours) | | | | | | | |
| --- | --- | --- | --- | --- | --- | --- | --- | --- |
| Medium | 1 | 2 | 4 | 8 | 12 | 18 | 24 | 48 |
| SGF | 0 | 1 | 1 | — | — | — | — | — |
| SIF | 6 | 10 | 17 | 27 | 35 | 46 | 55 | 80 |

EXAMPLE 4

|  | mg/capsule |
| --- | --- |
| Budesonide micronized | 0.5 |
| Sugar spheres | 286 |
| Auquacoat ECD 30 | 24.2 |
| Acetyltributyl citrate | 1.8 |
| Eudragit NE30D | 12.6 |
| Eudragit S100 | 12.6 |
| Talc | 12.6 |

Budesonide (0.90 g) was suspended in the Aquacoat ECD 30 dispersion (144 g) together with acetyltributyl citrate (1.82 g). The mixture was sprayed on to sugar spheres (510 g) in a fluid bed apparatus. The rate-limiting and enteric coating consisting of Eudragit S100 (22.5 g) and talc (22.5 g) suspended in the Eudragit NE30D dispersion (75.0 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 2.1 g of pellets were placed in the cells and the test were placed in the cells and the test commenced. For specified time periods fractions were collected and analyzed for budesonide by a liquid chromatographic method. The percentage dissolution at each time point was calculated. The results are shown in Table 4.

TABLE 4

Dissolution of budesonide of Example 4

| Medium | Percentage dissolution after (hours) | | | | | |
|---|---|---|---|---|---|---|
| | 1 | 2 | 4 | 8 | 12 | 18 |
| SGF | 1 | 1 | 3 | — | — | — |
| SIF | 7 | 15 | 29 | 50 | 67 | 84 |

Absorption Data for the Budesonide Formulation Prepared in Example 1

Each of two healthy volunteers took the formulation in Example 1 corresponding to 9 mg of budesonide. Blood samples were drawn at different time-points up to 48 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 1A. The absolute bioavailability was 10.8% and 9.6% for the two subjects, respectively. For comparison, the absolute bioavailability of a fast releasing budesonide capsule is 10 to 15%, and the mean absorption time is less than 2 hours. Of the dose absorbed about 30% and 55% was absorbed in the time interval 2–12 hours in the two subjects, respectively. Absorption in this time interval probably occurs during the passage of the formulation through ileum, caecum and proximal colon.

TABLE 1A

| Subj no. | Percentage absorption after (hours) | | | | | | |
|---|---|---|---|---|---|---|---|
| | 1 | 2 | 4 | 8 | 12 | 24 | 36 |
| 3 | — | 7 | 14 | 23 | 37 | 83 | 100 |
| 5 | 13 | 39 | 61 | 85 | 94 | 99 | 100 |

Absorption Data for the Budesonide Formulation Prepared in Example 2

Each of two healthy volunteers took the formulation in Example 2 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 2A. The absolute bioavailability was 3.1% and 2.3% for the two subjects, respectively. For comparison, the absolute bioavailability of a fast releasing budesonide capsule is 10 to 15%, and the mean absorption time is less than 2 hours. Of the dose absorbed about 68% and 67% was absorbed in the time interval 6–36 hours in the two subjects, respectively. Absorption in this time interval probably occurs during the passage of the formulation through caecum and colon-rectum.

TABLE 2A

| Subj no. | Absorption of budesonide of Example 2 | | | | | | | | |
|---|---|---|---|---|---|---|---|---|---|
| | Percentage absorption after (hours) | | | | | | | | |
| | 2 | 4 | 6 | 8 | 12 | 24 | 36 | 48 | 60 | 72 |
| 4 | 5 | 15 | 24 | 29 | 48 | 80 | 92 | 96 | 98 | 100 |
| 5 | 5 | 19 | 33 | 43 | 57 | 87 | 100 | | | |

Absorption Data for the Budesonide Formulation Prepared in Example 3

Each of two healthy volunteers took the formulation in Example 3 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 3A. The absolute bioavailability was 6.3% and 4.9% for the two subjects, respectively. For comparison, the absolute bioavailability of a fast releasing budesonide capsule is 10 to 15%, and the mean absorption time is less than 2 hours. Of the dose absorbed about 67% and 71% was absorbed in the time interval 6–36 hours in the two subjects, respectively. Absorption in this time interval probably occurs during the passage of the formulation through caecum and colon-rectum.

TABLE 3A

Absorption of budesonide of Example 3

| Subj no. | Percentage absorption after (hours) | | | | | | | | |
|---|---|---|---|---|---|---|---|---|---|
| | 2 | 4 | 6 | 8 | 12 | 24 | 36 | 48 | 60 | 72 |
| 1 | 6 | 16 | 27 | 35 | 53 | 83 | 94 | 98 | 99 | 100 |
| 3 | 1 | 2 | 6 | 16 | 28 | 57 | 78 | 91 | 97 | 100 |

Absorption Data for the Budesonide Formulation Prepared in Example 4

Each of two healthy volunteers took the formulation in Example 4 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 4A. The absolute bioavailability was 16.2% and 3.4% for the two subjects, respectively. For comparison, the absolute bioavailability of a fast releasing budesonide capsule is 10 to 15%, and the mean absorption time is less than 2 hours. Of the dose absorbed about 71% and 44% was absorbed in the time interval 6–36 hours in the two subjects, respectively. Absorption in this time interval probably occurs during the passage of the formulation through caecum and colon-rectum.

TABLE 4A

Absorption of budesonide of Example 4

| Subj no. | Percentage absorption after (hours) | | | | | | | | |
|---|---|---|---|---|---|---|---|---|---|
| | 2 | 4 | 6 | 8 | 12 | 24 | 36 | 48 | 60 | 72 |
| 1 | 3 | 16 | 24 | 36 | 56 | 86 | 94 | 98 | 99 | 100 |
| 2 | 8 | 33 | 51 | 62 | 72 | 89 | 95 | 97 | 99 | 100 |

What is claimed is:

1. A method for the prevention or treatment of a bowel disease selected from the group consisting of ulcerative colitis, Crohn's colitis in its active phase, Crohn's colitis in its chronic phase as relapse preventing therapy and Crohn's disease in the small intestine as relapse preventing therapy, which comprises the oral administration per 24-hour period of a controlled-release pharmaceutical formulation comprising 2–20 mg of a compound selected from budesonide and the 22-R epimer thereof and which will release the compound at the site of the disease to be treated, to a patient in need of such prevention or treatment.

2. A method according to claim 1, wherein the compound is budesonide.

3. A method according to claim 1, wherein the 2–20 mg of the compound administered in a 24-hour period are divided into 1 to 4 doses.

4. A method according to claim 3, wherein the compound is administered in a unit dose of from 0.25–20 mg.

5. A method according to claim 4, wherein the compound is administered in a unit dose of from 2–5 mg.

6. A method according to claim 4, wherein the compound is administered in a unit dose of 0.5, 1.0 or 2.0 mg.

7. A method according to claim 1, wherein the compound is the 22-R epimer of budesonide.

8. A method according to any one of claims 1–6 and 7, wherein the disease is ulcerative colitis.

9. A method according to claim 8, wherein the formulation is in a form which will release the compound in the colon.

10. A method according to claim 8, wherein the formulation is in a form which will release the compound over a period of from 25–50 hours.

11. A method according to claim 8, wherein the formulation is in a form which will release the compound over a period of from 25–50 hours.

12. A method according to any one of claims 1 to 6 and 7, wherein the condition to be treated is Crohn's disease of the ileum and the formulation is in a form which will release the compound in the small intestine.

13. A method according to claim 12, wherein the formulation is in a form which will release the compound over a period of from 1–50 hours.

14. A method according to claim 13, wherein the formulation is in a form which will release the compound over a period of from 5–10 hours.

* * * * *

UNITED STATES PATENT AND TRADEMARK OFFICE
CERTIFICATE OF CORRECTION

PATENT NO. : 6,423,340 B2
DATED : July 23, 2002
INVENTOR(S) : Ulmius

It is certified that error appears in the above-identified patent and that said Letters Patent is hereby corrected as shown below:

Title page,
Item [30], Foreign Application Priority Data,
Filing date should be -- Nov. 22, 1989 --.

Column 1,
Line 5, delete "field" and substitute therefor -- filed --.

Column 2,
Line 55, delete "11β," and substitute therefor -- 11β- --.
Lines 58-59, delete "11β, 21-dihydroxypregn-" and substitute therefor
-- 11β-hydroxypregn- --.

Column 5,
Line 31, insert "," after -- first --.
Line 44, delete "asterified" and substitute therefor -- esterified --.
Line 59, delete "polyethyleneglycols" and substitute therefor -- polyethylene glycols --.

Column 10,
Lines 62-63, delete "the test were placed in the cells and".

Column 14,
Line 15, "claim 8" should read -- claim 9 --.

Signed and Sealed this

Third Day of June, 2003

JAMES E. ROGAN
*Director of the United States Patent and Trademark Office*